US011579088B2

United States Patent
Bawendi et al.

(10) Patent No.: US 11,579,088 B2
(45) Date of Patent: Feb. 14, 2023

(54) DEVICE AND METHOD FOR IMAGING SHORTWAVE INFRARED FLUORESCENCE

(71) Applicants: Massachusetts Institute of Technology, Cambridge, MA (US); The General Hospital Corporation, Boston, MA (US)

(72) Inventors: Moungi G. Bawendi, Cambridge, MA (US); Oliver Thomas Bruns, Garching (DE); Jessica Ann Carr, Cambridge, MA (US); Klaus van Leyen, Medford, MA (US); Yi Zheng, Cambridge, MA (US); Marianne Aellen, Schüpfen (CH)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 766 days.

(21) Appl. No.: 16/083,603

(22) PCT Filed: Mar. 10, 2017

(86) PCT No.: PCT/US2017/021845
§ 371 (c)(1),
(2) Date: Sep. 10, 2018

(87) PCT Pub. No.: WO2017/160643
PCT Pub. Date: Sep. 21, 2017

(65) Prior Publication Data
US 2019/0079010 A1 Mar. 14, 2019

Related U.S. Application Data
(60) Provisional application No. 62/307,997, filed on Mar. 14, 2016.

(51) Int. Cl.
*G01N 21/64* (2006.01)
*A61B 5/00* (2006.01)

(52) U.S. Cl.
CPC ....... *G01N 21/6456* (2013.01); *A61B 5/0071* (2013.01); *G01N 21/6428* (2013.01); *A61B 2503/40* (2013.01); *G01N 2021/6439* (2013.01)

(58) Field of Classification Search
CPC .......... G01N 21/6456; G01N 21/6428; G01N 2021/6439; A61B 5/0071; A61B 2503/40
(Continued)

(56) References Cited

U.S. PATENT DOCUMENTS 5,733,721 A * 3/1998 Hemstreet, III . G01N 33/57407
435/6.14
6,665,556 B1 12/2003 Alfano et al.
(Continued)

FOREIGN PATENT DOCUMENTS

WO WO 2010/138738 A1 12/2010
WO WO 2012/039679 A2 3/2012

OTHER PUBLICATIONS

Santos, I. P., Caspers, P. J., Bakker Schut, T., van Doorn, R., Koljenović, S., & Puppels, G. J. (2015). Implementation of a novel low-noise InGaAs detector enabling rapid near-infrared multichannel Raman spectroscopy of pigmented biological samples. Journal of Raman Spectroscopy, 46(7), 652-660. (Year: 2015).*
(Continued)

*Primary Examiner* — Jason M Ip
*Assistant Examiner* — Renee C Langhals
(74) *Attorney, Agent, or Firm* — Wolf, Greenfield & Sacks, P.C.

(57) ABSTRACT

Systems and methods for measuring short wave infrared fluorescence and autofluorescent signals are disclosed. In
(Continued)

some embodiments, for example, a method may include exposing a portion of tissue that does not include a fluorescent probe to an excitation source of the tissue, wherein at least a portion of the tissue has an autofluorescence spectrum which includes wavelengths greater than 900 nm, and imaging the tissue with a detector that is sensitive to electromagnetic radiation with wavelengths greater than or equal to 900 nm. In certain other embodiments, a system comprises a fluorescent probe including a fluorescent component attached to a carrier, an excitation source, and a detector that detects a tail portion of the fluorescence of the fluorescent component. Methods associated with such a system are also disclosed.

23 Claims, 13 Drawing Sheets

(58) Field of Classification Search
USPC .......................................................... 600/476
See application file for complete search history.

(56) References Cited

U.S. PATENT DOCUMENTS

| | | | |
|---|---|---|---|
| 2007/0019208 A1* | 1/2007 | Toida | A61B 5/0066 356/497 |
| 2009/0137910 A1* | 5/2009 | Pyle | A61B 5/0084 600/478 |
| 2013/0296708 A1* | 11/2013 | Zuzak | G01J 3/0264 600/476 |
| 2015/0030542 A1* | 1/2015 | Singhal | A61K 49/0034 424/9.6 |
| 2015/0056142 A1* | 2/2015 | Tao | G01N 33/553 424/9.6 |
| 2015/0150459 A1* | 6/2015 | Werahera | A61B 8/0841 600/411 |

OTHER PUBLICATIONS

Terasaki, H., Inoue, Y., Sugano, N., Jibiki, M., Kudo, T., Lepäntalo, M., & Venermo, M. (2013). A quantitative method for evaluating local perfusion using indocyanine green fluorescence imaging. Annals of vascular surgery, 27(8), 1154-1161. (Year: 2013).*
IRDye Infrared Dyes Advancing Discovery With Infrared Imaging, LI-COR, https://www.ld.ru/w/licor/IRDye_brochure_web.pdf, date accessed—Oct. 28, 2021, wayback machine capture date—Dec. 22, 2014 (Year: 2014).*
International Search Report and Written Opinion dated Jun. 29, 2017 for Application No. PCT/US2017/021845.
International Preliminary Report on Patentability dated May 6, 2018 for Application No. PCT/US2017/021845.
Benson et al., Fluorescence properties of indocyanine green as related to angiography. Phys Med Biol. Dec. 1978;23(1):159-63.
Diao et al., Fluorescence imaging in vivo at wavelengths beyond 1500 nm. Angew Chem Intl Ed. Oct. 13, 2015;54(49):14758-62.
Naczynski et al., Rare-earth-doped biological composites as in vivo shortwave infrared reporters. Nat Commun. Jul. 22, 2013;4:2199(1-10).
Tsukasaki et al., A short-wavelength infrared emitting multimodal probe for non-invasive visualization of phagocyte cell migration in living mice. Chem Commun. Jan. 2014;50(92): 14356-9.
Wang et al., In vivo near-infrared autofluorescence imaging of pigmented skin lesions: methods, technical improvements and preliminary clinical results. Skin Res Technol. Feb. 2013;19(1):20-6. doi: 10.1111/j.1600-0846.2012.00632.x. Epub Jun. 22, 2012.

* cited by examiner

Mouse head room light reflectance

IRDye800-trastuzumab fluorescence

IRDye800-PEG fluorescence

False-color fluorescence image

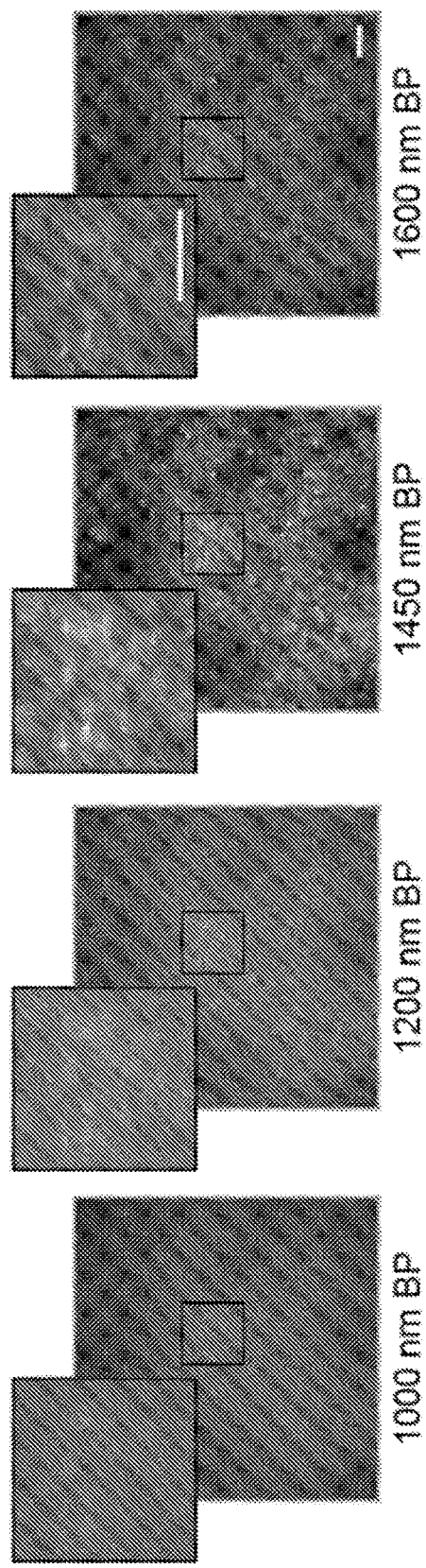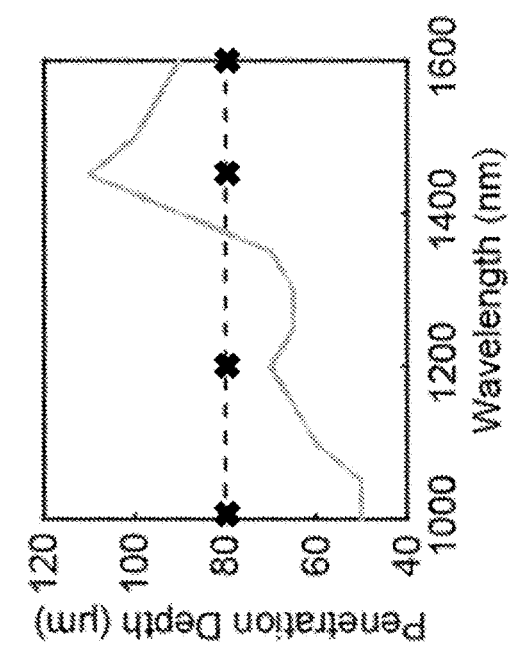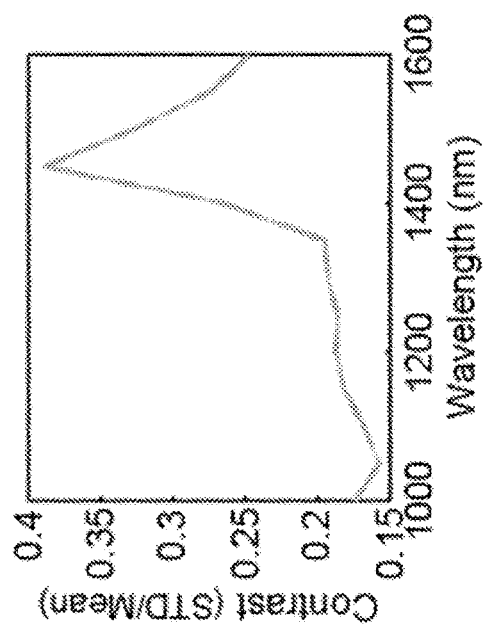
Fig. 18A 1000 nm BP
Fig. 18B 1200 nm BP
Fig. 18C 1450 nm BP
Fig. 18D 1600 nm BP
Fig. 19
Fig. 20

DEVICE AND METHOD FOR IMAGING SHORTWAVE INFRARED FLUORESCENCE

CROSS-REFERENCE TO RELATED APPLICATIONS

This application is a national stage filing under 35 U.S.C. 371 of International Patent Application Serial No. PCT/US2017/021845, filed Mar. 10, 2017, which claims the benefit of priority under 35 U.S.C. § 119(e) of U.S. provisional application Ser. No. 62/307,997, filed Mar. 14, 2016, each of which is incorporated by reference here in its entirety.

FEDERALLY SPONSORED RESEARCH

This invention was made with Government support under EB015871 awarded by the National Institutes of Health, and W911NF-13-D-0001 awarded by the U.S. Army Research Office. The Government has certain rights in the invention.

BACKGROUND

Current in vivo imaging technologies fail to provide high resolution, desirable penetration depths, and sensitivity simultaneously, which limits their widespread adoption for identifying diseases. For example, high resolution and high sensitivity imaging is straightforward on single cells using visible light imaging techniques. However, when imaging whole animals and their tissues, resolution and sensitivity of subsurface tissue features are drastically reduced due to scattering and absorption of light by surrounding tissue. Another major limitation of conventional in vivo imaging technologies is the intense background autofluorescence of tissue at the same wavelengths as the emission wavelengths of the fluorescent probes used to detect various conditions. This overlap of autofluorescence with the expected emission wavelengths of the associated fluorescent probes inhibits disease detection. In one such example, traditional imaging with visible and near infrared wavelengths suffers from poor contrast against the background autofluorescence signals from normal cells and tissues.

SUMMARY

In one embodiment, a system includes a fluorescent probe with a fluorescence spectrum including a fluorescence peak below 900 nm and at least a portion of a tail of the fluorescence spectrum at a wavelength greater than 900 nm. The system also includes an excitation source that emits electromagnetic radiation at wavelengths less than 900 nm and a detector that detects fluorescence emitted from the fluorescent probe. The detector detects electromagnetic radiation with wavelengths greater than 900 nm.

In another embodiment, a system includes a fluorescent probe including a fluorescent component attached to a carrier. The fluorescent component fluoresces over a first range of wavelengths and the carrier autofluoresces over a second range of wavelengths at least partially overlapping the first range. Further, a ratio of an intensity of a tail portion of the first range of wavelengths and a corresponding intensity of the carrier autofluorescence is greater than a ratio of an intensity of a peak fluorescent emission wavelength of the fluorescent component and corresponding intensity of the carrier autofluorescence. The system also includes an excitation source that emits electromagnetic radiation within an absorption spectrum of the fluorescent component and a detector that detects electromagnetic radiation within the tail portion of the first range of wavelengths.

In yet another embodiment, a method includes: exposing a portion of tissue including a fluorescent probe to an excitation source of the fluorescent probe, wherein the fluorescent probe has a fluorescence spectrum including a peak below 900 nm and at least a portion of a tail of the fluorescence spectrum has a wavelength greater than 900 nm; and imaging the tissue with a detector that is sensitive to electromagnetic radiation with wavelengths greater than or equal to 900 nm.

In another embodiment, a method includes: exposing a portion of tissue including a fluorescent probe to an excitation source of the fluorescent probe, wherein the fluorescent probe includes a fluorescent component attached to a carrier, wherein the fluorescent component fluoresces over a first range of wavelengths and the carrier autofluoresces over a second range of wavelengths at least partially overlapping the first range, wherein a ratio of an intensity of a tail portion of the first range of wavelengths and a corresponding intensity of the carrier autofluorescence is greater than a ratio of an intensity of a peak fluorescent emission wavelength of the fluorescent component and corresponding intensity of the carrier autofluorescence; and detecting the tail portion of the fluorescence of the fluorescent component.

In yet another embodiment, a method includes: exposing a portion of tissue that does not include a fluorescent probe to an excitation source of the tissue, wherein at least a portion of the tissue autofluorescence spectrum includes wavelengths greater than 900 nm; and imaging the tissue with a detector that is sensitive to electromagnetic radiation with wavelengths greater than or equal to 900 nm.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various nonlimiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIGS. 18A-18D are fluorescence images taken of quantum dot labeled cells of a mouse liver at different wavelengths;

FIG. 19 is a graph of observed contrast plotted as a function of wavelength; and FIG. 20 is a graph of penetration depth as a function of wavelength.

DETAILED DESCRIPTION

Figure 1:
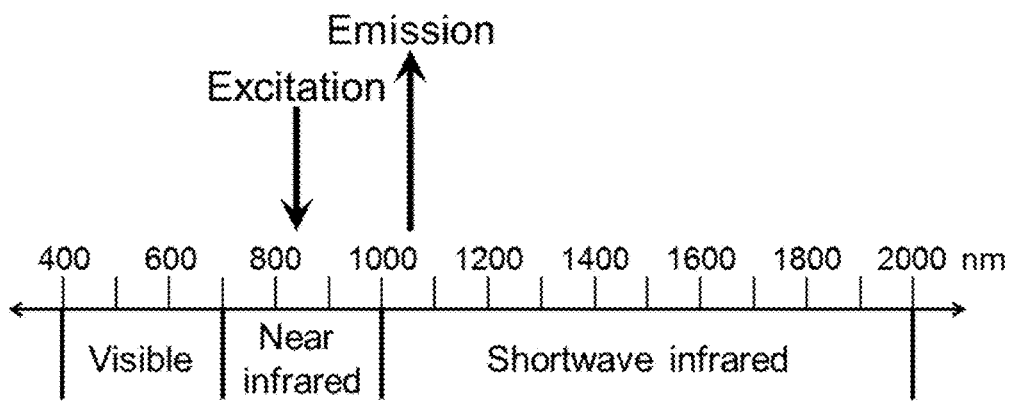
FIG. 1 is a graph of an excitation and corresponding emission wavelength.

The inventors have recognized that despite the widespread use of fluorescent probes including a fluorescent component, such as a fluorescent dye, for fluorescence-based pathological determinations, applications have been limited by the failure of current in vivo imaging technologies to provide high resolution, sufficient penetration depths, and sensitivity simultaneously. For example, straightforward, cell-specific imaging is achievable using visible and near infrared imaging techniques, but high sensitivity and resolution in tissues are intrinsically limited by multiple factors that arise from scattering and absorption of light by surrounding tissue. Another major limitation in studying signals of fluorescent probes, and their pathological implications, has been the difficulty of achieving sufficient contrast using these fluorescent probes against the background autofluorescence signal emitted by normal cells and tissues.

In view of the above, the inventors have recognized the benefits associated with imaging in the short wave infrared (SWIR) spectral region to avoid the shortcomings of imaging in the visible and near infrared spectrums. Without wishing to be bound by theory, the longer imaging wavelength reduces photon scattering processes, thus maximizing transmission of the imaged light through the tissue within the SWIR spectrum. Thus, imaging in this frequency range results in significantly improved resolution and signal intensity for a given penetration depth. In addition, SWIR radiation exhibits sufficient tissue penetration depths to noninvasively interrogate changes in subsurface tissue features, whereas visible imaging techniques are typically limited to imaging superficial biological structures. For example, in some embodiments, SWIR may permit penetration depths of up to 2 mm or more with a sub 10 micrometer resolution, though instances where SWIR permits larger penetration depths with a different resolution are also contemplated. Further, unlike the visible and near-infrared regions, the SWIR regime contains very little background autofluorescence from healthy tissues, especially in skin and muscle. This reduced autofluorescence signal improves the contrast with the corresponding fluorescence signal from a fluorescent probe and/or autofluorescence from diseased tissue enabling easier distinction between pathological and non-pathological biological structures. The reduced light scattering, enhanced light transmission, and suppressed background autofluorescence all combine to enable imaging and detection methods with increased contrast, resolution, and sensitivity as compared to more typical imaging methods.

In addition to the above, the fluorescent emission of many fluorescent components, such as fluorescent dyes used in fluorescent probes for medical purposes, was previously thought to be sufficient for imaging and detection of conditions only in the visible and near infrared spectrums. Therefore, the use of these fluorescent components has been restricted to uses in the visible and near infrared spectrums because it was thought the tail signal, which is less bright, was insufficient for imaging and detection purposes. However, as detailed below, the inventors have recognized that many of these fluorescent components actually fluoresce substantially at wavelengths within the SWIR spectrum as well. This misconception was due in part to the prior sensors used to measure the spectrums for these compounds being insensitive to emissions within the SWIR spectrum. Therefore, even though many of these fluorescent compounds exhibit peaks that are outside of the SWIR spectrum, they still exhibit sufficient fluorescence signals within the SWIR spectrum to be usable with devices and methods that measure SWIR fluorescence signals for either detection and/or diagnostic purposes as detailed further below. Further, coupled with the decreased autofluorescence signal of the healthy tissue, this may lead to an overall increase in the contrast of diseased tissue relative to the background autofluorescence signal for imaging and diagnostic purposes.

In view of the above, the inventors have recognized the benefits associated with an optical imaging method and system for detecting SWIR fluorescence from various types of fluorescent probes. In one such embodiment, a fluorescent probe includes a peak fluorescence and absorption spectrum that is at least partially outside of the SWIR spectrum. Further, the fluorescent probe includes a tail that at least partially extends into the SWIR spectrum. In such an embodiment, a corresponding imaging or diagnostic device may include an excitation source that emits electromagnetic radiation within the absorption spectrum of the fluorescent probe and outside of the SWIR spectrum. The device also includes a detector that detects fluorescence emitted from the fluorescent probe within the tail portion of the spectrum located in the SWIR spectrum.

In another embodiment, the inventors have recognized that imaging of a fluorescent probe in a particular spectrum, such as the SWIR spectrum, may reduce, and/or substantially eliminate, an autofluorescence signal associated with a carrier of the fluorescent probe. Therefore, in some embodiments, a fluorescent probe may include a fluorescent component attached to a carrier where the fluorescence spectrum of the carrier at least partially overlaps the autofluorescence spectrum of the carrier. Further, a ratio of an intensity of the fluorescence spectrum and a corresponding intensity of the carrier autofluorescence (i.e. contrast) is greater in a tail portion of the fluorescence spectrum than at a peak fluorescent emission wavelength of the fluorescence spectrum. Consequently, in such an embodiment, a corresponding device may include an excitation source that emits electromagnetic radiation within an absorption spectrum of the fluorescent component and a detector that detects electromagnetic radiation within the tail portion of fluorescence spectrum.

In yet another embodiment, the inventors have recognized that the increased autofluorescence signal of diseased tissue relative to healthy tissue in the SWIR spectral region may be used to identify a tissue state of imaged tissue and/or a patient condition. Consequently, in some embodiments, tissue that does not include a fluorescent probe, or other marker, is exposed to an autofluorescence excitation source of the tissue in a first spectral region. The autofluorescence signal of the tissue is then detected using a detector that is sensitive to electromagnetic radiation in a second different spectral region. In some instances the excitation source emits in the near infrared (NIR) spectral region and the detector is sensitive to electromagnetic radiation in the SWIR spectral region.

In view of the above, in some embodiments, a device may include an excitation source that is configured and arranged to expose tissue, that may or may not include a fluorescent probe, to electromagnetic radiation within an adsorption spectra of the fluorescent probe and/or tissue. Depending on the particular probe, the excitation source may emit electromagnetic radiation within a particular band of the absorption spectra of the fluorescent probe and/or tissue. Alternatively, the excitation source may emit electromagnetic radiation over the entire absorption spectrum of the fluorescent probe as the disclosure is not so limited. Regardless, in some embodiments, the excitation source may emit electromagnetic radiation that includes wavelengths greater than or equal to 300 nm, 350 nm, 400 nm, 500 nm, 600 nm, 700 nm, 800 nm or any other appropriate wavelength. Additionally, the excitation source may emit electromagnetic radiation within an absorption spectrum that includes wavelengths less than or equal to 900 nm, 800 nm, 700 nm, and/or any other appropriate wavelength. Combinations of the above range of wavelengths are contemplated including, for example, an excitation source that emits electromagnetic radiation between or equal to 300 nm and 900 nm. While particular ranges and combinations of wavelengths are noted above, it should be understood that other wavelengths for an excitation source, both greater than and less than those noted above, are also contemplated as the disclosure is not so limited.

In one embodiment, a device includes a detector for detecting a portion of a tail portion of a fluorescence spectrum. While this tail portion may correspond to any range of wavelengths depending on the particular application, in one embodiment, the tail portion includes wavelengths greater than or equal to about 900 nm, 1000 nm, 1100 nm, 1200 nm, 1300 nm, 1400 nm, 1500 nm, 1600 nm and/or any other appropriate wavelength. Correspondingly, the tail portion may include wavelengths that are less than or equal to about 2000 nm, 1600 nm, 1500 nm, 1400 nm, 1300 nm, and/or any other appropriate wavelength. Combinations of the above noted wavelength ranges of a tail portion of a fluorescence spectrum and the ranges a corresponding detector is sensitive to are contemplated. For example, a detector, as well as any associated filters or other optical components, may be configured and arranged to detect a tail portion of a fluorescence spectrum that is between or equal to about 900 nm and 2000 nm. Of course, tail portions of a spectrum, and the detectors used to measure them, that exhibit wavelengths, both smaller and greater than those ranges noted above are contemplated as the disclosure is not so limited. The above noted ranges may also be applied to measuring the autofluorescence signals of healthy and diseased tissues as well.

In the above noted embodiments, a corresponding peak emission wavelength of a fluorescent probe may be at smaller wavelengths than a tail portion of the fluorescent probe. For instance, in some embodiments, a peak wavelength of a fluorescent probe may include, but is not limited to, wavelengths less than or equal to 900 nm.

Fluorescence spectra typically include one or more peak fluorescence intensities. These intensities may either be a local and/or global peak that is greater than the intensity of the fluorescence spectrum at surrounding wavelengths. Further, while a spectrum is continuous and a peak will span a range of wavelengths, a peak is generally described in reference to the wavelength at which the largest fluorescence intensity is measured. Additionally, while it can be argued that a fluorescence spectrum is continuous over all wavelengths, just with a vanishingly small detectable signal, for purposes of this application, wavelengths where the measured fluorescence and/or autofluorescence intensities are less than or equal to 0.01%, 0.1%, 1%, or other appropriate percentage of a maximum peak intensity and/or that are not greater than a background noise of a measured fluorescence signal are not considered as being within a fluorescent and/or autofluorescent spectrum wavelength range, let alone a tail portion of a spectrum, for a particular fluorescent probe and/or tissue.

In addition to the above, in some embodiments, a tail portion of a spectrum may be described as corresponding to a portion of the spectrum removed from a global peak of the spectrum. Also, in some embodiments, a tail portion of a spectrum may be described relative to a percentage of an area of a fluorescent spectrum at wavelengths greater than a global peak. For example, in some embodiments, the tail portion of a fluorescent spectrum may be greater than or equal to 1%, 5%, 10%, 20%, or any other appropriate percentage of the area of a fluorescent spectrum. Correspondingly, depending on the location of the spectrum peak, a tail portion of a fluorescence spectrum may be less than or equal to about 70%, 60%, 50%, 40%, 30%, 20%, or any other appropriate percentage of the area of the fluorescence spectrum. Combinations of the above are contemplated including, for example, a tail portion of the fluorescence spectrum that is between about 1% and 40% of the area of the fluorescence spectrum.

As noted previously, in some embodiments, a sensitivity of a fluorescent probe, as well as the associated device and method, are limited due to the autofluorescence of an associated carrier. Therefore, in some embodiments, it may be desirable to limit the detection of wavelengths for the fluorescent probe to regions of the carrier's autofluorescence spectrum that are removed from the peak autofluorescent emission wavelength of the carrier to help improve the contrast of the fluorescent probe. In one such embodiment, a peak autofluorescent emission wavelength of a carrier may be less than or equal to about 900 nm, 800 nm, 700 nm, or any other appropriate wavelength. Correspondingly, the peak autofluorescent emission wavelength of the carrier may be greater than or equal to about 400 nm, 500 nm, 600 nm, 700 nm, or any other appropriate wavelength. Combinations of the above ranges are contemplated including, for example, a peak autofluorescent emission wavelength of the carrier between or equal to about 400 nm and 900 nm.

Depending on the desired application of the disclosed methods and devices, it may be desirable to either display, and/or further process, a fluorescence and/or autofluorescence signal obtained by a detector. Therefore, in one embodiment, a detector may output a detected fluorescence and/or autofluorescence signal from the fluorescent probe located within tissue, and/or an autofluorescence signal of the tissue itself, to a computing device for further evaluation as detailed below. In addition, or alternatively to the above, the detector may output the detected fluorescence and/or autofluorescence signals to an associated display such as a monitor or printer. This display may either be separate from an imaging or diagnostic device or it may be integrated therewith as the disclosure is not so limited.

In embodiments, where a fluorescence or autofluorescence signal is output to a computing device, one or more actions may be taken with the received information. For example, in some embodiments, the computing device may either store the information in associated memory for later processing and/or communicate the information to a server, a separate computing device connected to the system, and/or transmit the information to a remotely located computing device for further processing, storage, and/or other handling of the information. In either case, in some embodiments, it may be desirable to process the received signal to determine a condition of the tissue and/or subject. For example, a field of view (FOV) of the detector may include a plurality of pixels that capture a fluorescence and/or autofluorescence signal from tissue the detector is oriented towards. The intensity of the detected signal for either each pixel, or groupings of pixels, may be compared to athreshold intensity. Pixels meeting, or exceeding, this threshold intensity may be identified as exhibiting a particular tissue state or subject condition.

Tissue states that a threshold intensity may indicate depending on the particular application include, but are not limited to: cancerous or cancer-related tissues; cirrhotic tissues; fibrotic and scarred tissue; radiation-treated tissues; inflamed tissues; aged tissues; stressed tissues; atherosclerotic lesions and plaques in vessels or tissues; neurodegenerative disease affected tissues, e.g. Alzheimer's disease, Alzheimer's Plaques, Parkinson's disease; agiography, including angiography of the eye and the following specific applications such as acute posterior multi-focal placoid pigment epitheliopathy, exudative senile macular degeneration, hemorrhagic detachment of retinal pigment epithelium, retinal hemorrhage, retinal neovascularization, serous detachment of retinal pigment epithelium, Behcet's disease (Behcet's syndrome), choroidal melanoma; critical limb ischemia, diabetic macular edema, Drusen differentiation, macular schisis, parasagittal meningioma, prediction of post-operative thrombosis in the internal jugular vein, prediction of wound complications in ventral hernia repair, sarcoidosis, scleritis and posterior scleritis, sentinel lymph node mapping, spinal dural arteriovenous fistula, Vogt-Koyanagi-Harada disease, and other appropriate uses for angiography; as well as other applicable diseased, abnormal, or other tissue states of interest. Alternatively, the threshold intensity may be used to discriminate subject conditions such as a cirrhotic liver versus a healthy liver. The disclosed methods and systems may also be used to determine tissue perfusion, as may be done during reconstructive surgeries and bypass surgeries, using the detected fluorescence intensity from an image of the tissue of interest versus a predetermined threshold intensity.

In addition to the above, in some embodiments, the disclosed methods and systems may be used to identify one or more structures or conditions based on a difference in an expected background tissue autofluorescence signal intensity versus a detected autofluorescence signal intensity. For example, either a measured and/or predetermined background autofluorescence signal intensity of a particular type of tissue may be determined, which in some instances may be a homogenous background autofluorescence signal intensity. In contrast, a structure of interest may include one or more components that absorb fluorescence within the desired range of wavelengths for the detected autofluorescence signal intensity. For instance, in one specific embodiment, a structure may be filled with, or largely composed of, water (e.g. cysts or abscesses), which may reduce the expected fluorescence signal intensity because these structures include water which strongly absorbs fluorescence within the SWIR frequency ranges. The structures may then be detected by determining if the detected autofluorescence signal intensity is equal to or below a threshold autofluorescence intensity value that is less than the expected background autofluorescence signal intensity. Additionally, the relatively homogenous background autofluorescence signal may help to provide improved contrast when imaging these fluorescence signal absorbing structures.

While the above embodiment is described relative to autofluorescence, embodiments in which a fluorescent probe is imaged in a wavelength range where one or more components of a structure of interest absorb fluorescence are also contemplated. Accordingly, similar to the above, this may provide an improved contrast for the imaged structures and may also enable the detection of the desired structures by determining if a fluorescence signal intensity is less than a threshold fluorescence intensity value that is less than an expected background fluorescence signal intensity.

In the above embodiments, water has absorption peaks which may be used to improve autofluorescence and/or fluorescence imaging contrast and/or detection near 980 nm, 1150 nm, 1450 nm, and 1900 nm. Accordingly, imaging with improved contrast and/or detection of structures including increased amounts of water relative to the surrounding tissue may be conducted in frequency ranges within 25 nm, 50 nm, or any other appropriate range of the above wavelengths. For example, imaging of autoflouorescence and/or fluorescence signals emitted from tissue and/or a probe of interest may be conducted in a frequency range between or equal to 1425 nm and 1475 nm, 1400 nm and 1500 nm, or any other appropriate range. Of course, while structures including water have been noted above, embodiments in which structures including a different component in larger or smaller amounts than surrounding tissue that absorbs in a particular frequency range of interest may also be used as the disclosure is not so limited.

While specific types of tissue states and subject conditions are noted above, it should be understood that the currently disclosed systems and methods may be applied to any appropriate type of subject condition and/or tissue state. Additionally, while intensity thresholding may be used in some embodiments, in other embodiments, the disclosed systems and methods may be used without intensity thresholding such as for example, to simply provide an image with better contrasting, as the disclosure is not so limited.

In the above noted embodiments, a computing device comparing the detected fluorescence and/or autofluorescence intensities of the plurality of pixels to a threshold intensity may assign a tissue state and/or subject condition to one or more pixels meeting, or exceeding, the threshold intensity. This tissue state or condition may then be presented on a display (e.g. an image depicting the tissue states of the imaged tissue), stored within the memory of the computing device, transmitted to another computing device, output as a diagnostic result (i.e. a subject condition is present or not), and/or used in any other appropriate fashion.

It should be understood that the various devices and methods described herein may be used on any appropriate type of tissue and for any number of different applications. For example, an imaging and/or diagnostic device may be constructed and arranged to both expose tissue within an object to an excitation source of a fluorescent probe and/or the tissue itself for subsequently detecting a fluorescence and/or autofluorescence signal from the object. However, depending on the particular use of the device, the object may correspond to a number of different surfaces and/or configurations. In one such embodiment, the object is the body of a subject and the imaging and/or diagnostic device performs noninvasive imaging and/or detection on the subject's entire body at once and/or a subpart of the subject's body (i.e. torso, arm, leg, head, or sub-portion thereof). Alternatively, the object may be a surgical bed of a subject during an operation such as the tissue exposed during an extraction of a cancerous tumor. In yet another embodiment, the object may correspond to an excised piece of tissue (e.g. an excised tumor including tumor margins that are imaged to detect any residual cancer associated cells). Of course, other specific applications of an imaging and/or diagnostic device are also contemplated as the disclosure is not so limited to only those applications noted herein.

It should be understood that any detector that is sensitive to the desired ranges of electromagnetic radiation described herein may be used with the disclosed devices and methods. However, in one embodiment, a detector used within an imaging and/or diagnostic device may be an InGaAs (Indium gallium arsenide) detector, Germanium detector, MCT (Mercury cadmium telluride) detector, bolometers, and/or any other appropriate detector that is sensitive to the range of electromagnetic wavelengths of interest. Further, it should be understood that a detector is not limited to only these types of detectors, and in some instances may be a combination of detectors covering a range of wavelengths that may be within the noted wavelength ranges, and/or may extend outside of the described ranges, as the disclosure is not so limited.

A fluorescent probe may correspond to any appropriate compound capable of fluorescing and providing a desired contrast within tissue to help discriminate a desired tissue state and/or subject condition. In one embodiment, a fluorescent probe includes a fluorescent component such as a fluorescent dye. Appropriate fluorescent dyes include, but are not limited to, indocyanine green (ICG), Fluorescein, methylene blue, cyanine5 (Cy5), cyanine5.5 (Cy5.5), cyanine7 (Cy7), cyanine7.5 (Cy7.5), cypate, silicon rhodamine, 5-ALA, IRDye 700, IRDye 800CW, IRDye 800R5, E350 (e.g especially E350d), squarylium dyes, phthalocyanines, porphyrin derivatives, borondipyrromethane (BODIPY) dyes, and/or other food additives as well as many other dyes. Further, in some embodiments, these fluorescent components may fluoresce at shortwave infrared wavelengths in addition to other possible spectral ranges.

In addition to including a fluorescent component, a fluorescent probe may target a desired type of tissue or other biological feature within a subject's body in a number of different ways. In one such embodiment, a fluorescent probe may target a particular type of cell, such as cancer and cancer associated cells. Alternatively, in another embodiment, the fluorescent probe may simply be used in applications where it preferentially clears from some tissues while remaining in other tissues as might occur within a tumor surrounded by more vascularized tissue that clears the probe more quickly. Alternatively, fluorescent probes may be used to highlight the vasculature structure of the animal, which require long blood circulation times and slow clearing of the probes. Furthermore, the probes might be injected into a tumor to highlight the draining lymphatics and lymph nodes. Another use would be infusion into the bladder through a catheter to highlight the urinary tracts, e.g. ureters during operations. Another use is the injection up to 2 weeks prior to an operation in which case malignant and benign lesions in the liver might be differentially stained. Another application would be the intravenous injection and subsequent clearance through the liver into bile and the gastro-intestinal tract which would help to highlight disease conditions of the gallbladder, pancreas, as well as the small and large intestines.

In some embodiments, a fluorescent probe may also include a carrier that a fluorescent component is bonded to. For example, appropriate carriers include, but are not limited to, carbon nanotubes, nanoparticles (e.g. gold nanoparticles, indium arsenide-based or lead sulfide-based nanoparticles, silica nanoparticles, liposome nanoparticles), antibodies, proteins, DNA, small molecules, or any other type of particle, substrate, or compound that the fluorescent component is associated with. Additionally, the fluorescent component may be bonded to the carrier using any appropriate method as known in the art.

It should be understood that the specific amount and effect of a particular fluorescent probe will vary depending on the particular probe being used, the size of the subject, and the application it is being used for. Therefore, when a fluorescent probe is present in a particular location in an "effective amount" it means a concentration of the fluorescent probe is greater than or equal to a trace amount and is present in a concentration that is sufficient for achieving a desired purpose, such as, for example, permitting detection of the fluorescent probe in a subject for diagnostic purposes, imaging purposes, and/or to enhance a treatment of a disease or condition in a subject. In some embodiments, a particular fluorescent probe is used as a diagnostic or imaging compound such that its presence at a particular location is indicative of a particular condition of a subject.

The methods and devices described herein may be used for a number of different applications including noninvasive imaging of tissue using fluorescent probes while providing much higher resolution and sensitivity compared to comparable near infrared imaging techniques. This has huge implications in detecting and monitoring fluorescent probes in many clinical situations. Additionally, the ability to image autofluorescence of tissues noninvasively with sufficient contrast to delineate between abnormal and healthy biological structures is a major advance, and may accelerate investigations into mechanisms of disease or serve as a diagnostic medical device. For example, the described devices and methods using SWIR fluorescence and autofluorescence may enable quick and noninvasive assessment of the status of autophagy and/or other conditions in research animals and subjects.

Turning now to the figures, several nonlimiting embodiments are described in further detail. However, it should be understood that the current disclosure is not limited to only those specific embodiments described herein. Instead, the various disclosed components, features, and methods may be arranged in any suitable combination as the disclosure is not so limited.

FIG. 1 illustrates a range of different wavelengths corresponding to the different visible, near infrared, and short-wave infrared spectral regions. The figure also illustrate the exposure of tissue to an excitation wavelength, or range of wavelengths, below 900 nm and a corresponding fluorescent and/or autofluorescent emission that occurs above 900 nm.

Figure 2:
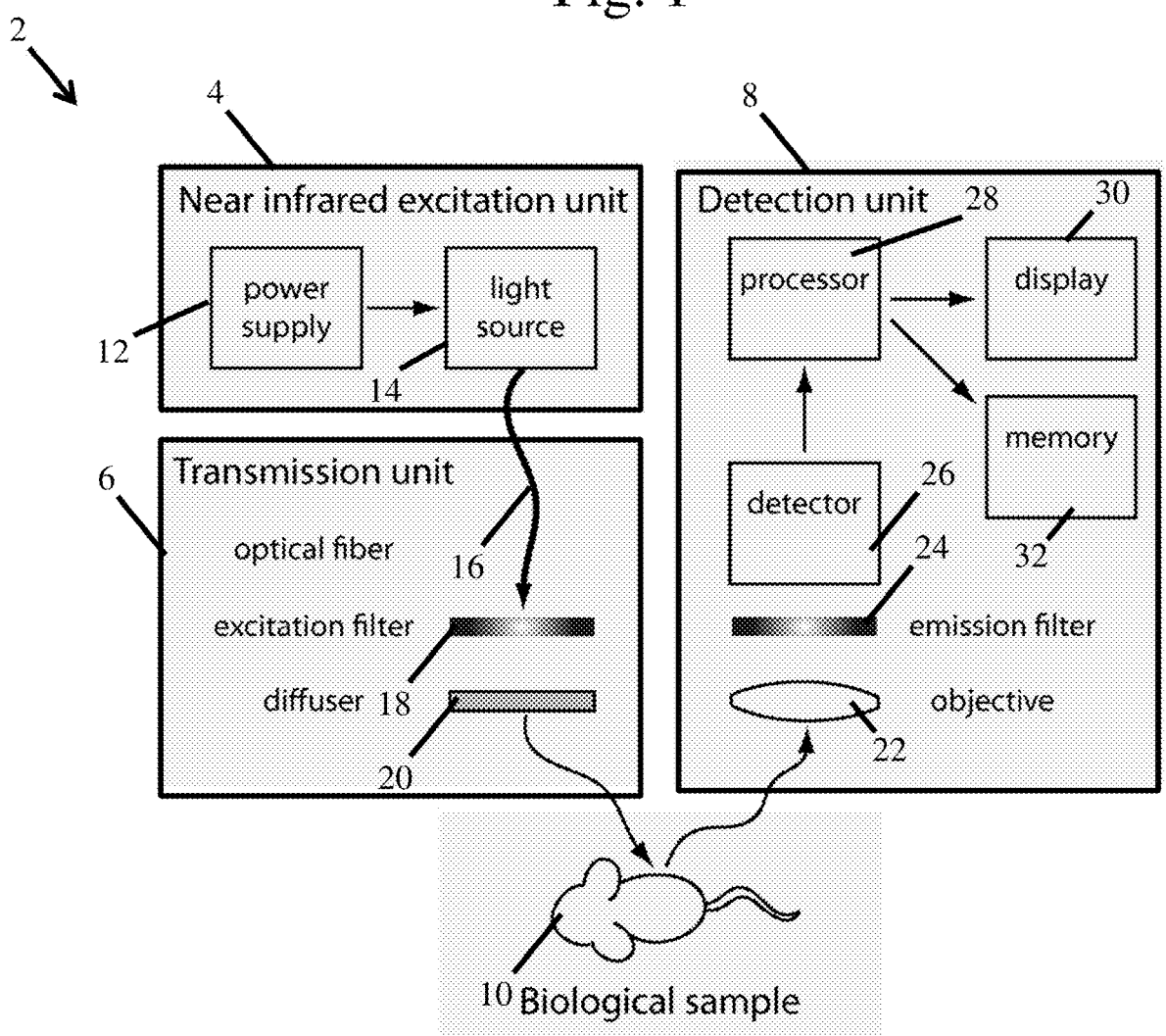
FIG. 2 is a schematic representation of an excitation unit, transmission unit, and corresponding detection unit according to one embodiment.

FIG. 2 depicts an imaging and/or diagnostic system 2. The system includes an excitation unit 4, a transmission unit 6, and a detection unit 8. As described further below, the excitation and transmission units expose a portion, or subportion of an object 10, such as the body of a subject, subportion of a subject's body, a surgical bed, and/or excised tissue, to an excitation wavelength, or range of wavelengths. Depending on the particular application, the object may either include a fluorescent probe located within the tissue of the object and/or there may not be a fluorescent probe and the excitation wavelengths may be excitation wavelengths of the tissue of the object itself. After exposing the object to the excitation wavelengths, the detection unit then detects and processes a fluorescent signal that is emitted from the object in response to the excitation wavelength. The components and interactions of these units and the object are detailed further below.

For the sake of clarity, the embodiments described below are primarily described for a device that is used for exciting and subsequently detecting fluorescence from a fluorescent probe located within the tissue of an object. However, it should be understood that the description is also applicable to embodiments where the excitation source is configured for exciting autofluorescence from the tissue of the object and detecting the resulting autofluorescence. Additionally, embodiments in which both phenomenon occur simultaneously and are both used in determining a tissue state and/or subject condition are also contemplated as the disclosure is not so limited.

In the illustrated embodiment, an excitation unit 4 may include a power source 12 that provides power to an excitation source 14. The excitation source may emit any desired range of wavelengths either within, and sometimes extending out of, an absorption spectrum of the fluorescent probe located within the tissue of the object 10. Any appropriate type of excitation source may be used including, but not limited to, a laser, light emitting diode, halogen based emitters, or any other appropriate source of electromagnetic radiation within a desired spectral band. The excitation source is optically coupled to the transmission unit 6 via any appropriate optical coupling 16 including, but not limited to, optical fiber bundles, a light pipe, a planar light guide, an optically clear path, or any other appropriate way of coupling the excitation source to the transmission unit. Regardless of the specific coupling, in the depicted embodiment, the optical coupling routes the electromagnetic radiation from the excitation source to an excitation filter 18, or set of filters. Depending on the desired excitation wavelengths and the type of source used, the filter may be a combination of low and/or high pass filters to provide electromagnetic radiation within a desired spectrum. For example, the filters may exclude electromagnetic wavelengths above and/or below a desired fluorescence spectrum wavelength or other undesirable excitation wavelengths. In some embodiments, the emitted electromagnetic radiation may then pass through a diffuser 20 to aid in spreading the excitation light across the object.

Once the excitation source has been exposed to the object, a fluorescent probe within the tissue of the object, and/or the tissue itself, fluoresces emitting electromagnetic radiation within a predetermined fluorescence spectrum towards the appropriately configured and arranged detection unit 8. In the depicted embodiment, the detection unit may include an objective lens 22 to appropriately image the object 10 onto an optically coupled detector 26 that includes a plurality of pixels that image and/or detect an intensity signal from the corresponding portions of the imaged object. Somewhere along the optical path between the object and the detector, one or more filters 24 may be located to exclude reflected excitation light from being detected by the detector. While the detector may be sensitive to any appropriate range of electromagnetic wavelengths, in some embodiments, the detector is sensitive to the ranges of wavelengths described herein including, but not limited to, the short wave infrared spectral range.

Once a fluorescent signal and/or autofluorescent signal have been detected by the detector 26, the detector may output the signal to a processor 28. The processor may then appropriately process the information as previously described to determine whether the detected signal corresponds to a particular tissue state and/or subject condition. This information may be determined for each pixel either for a single captured image and/or continuously in real time as might occur during imaging of a surgical procedure. The processed information may then be displayed as an image on a display 30 and/or stored within a memory 32 for subsequent viewing and/or usage.

Figure 3:
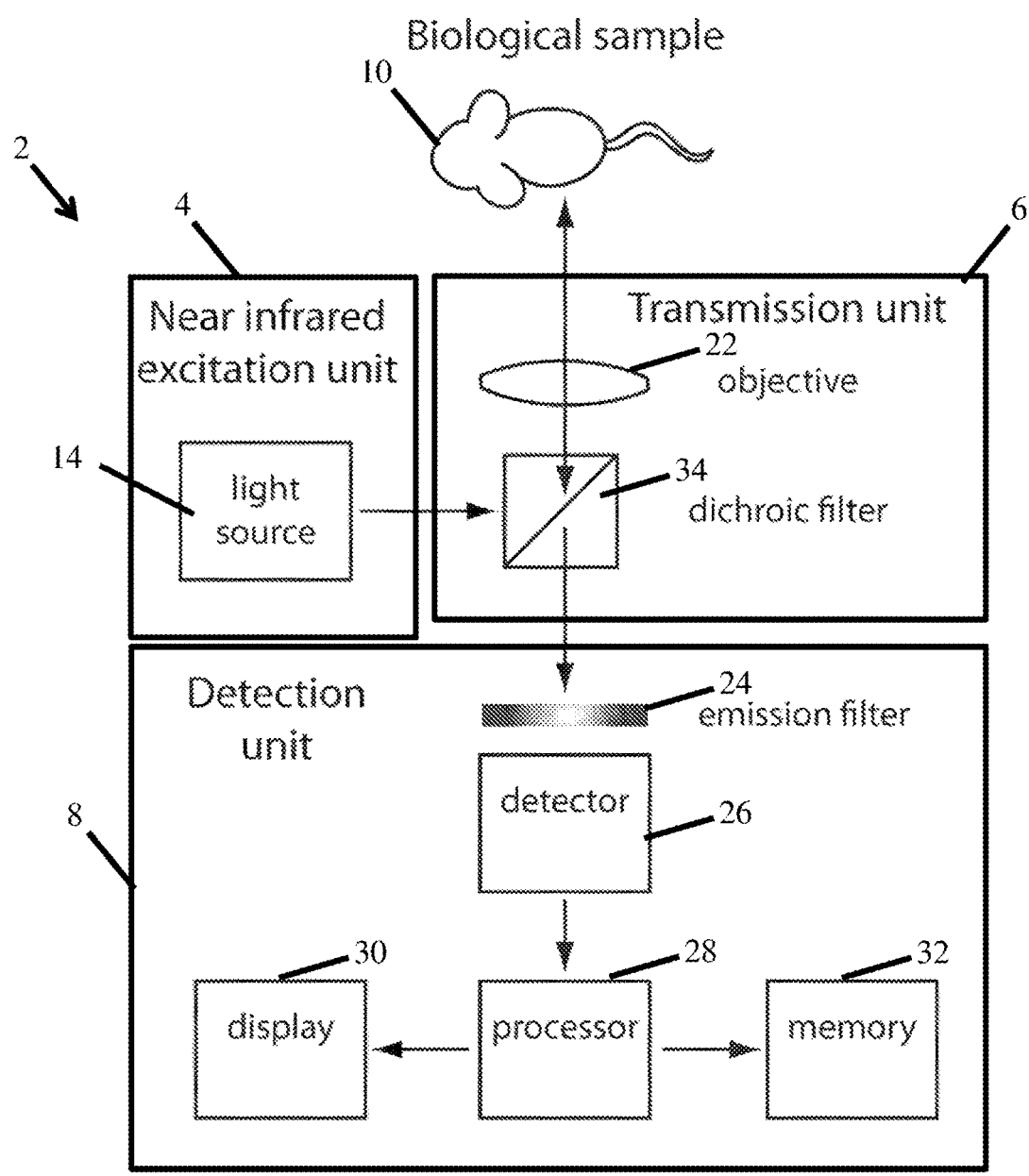
FIG. 3 is a schematic representation of an excitation unit, transmission unit, and corresponding detection unit according to one embodiment.

FIG. 3 presents another system similar to that shown in FIG. 2. However, in the depicted embodiment, the device includes a modified transmission unit 6 that includes a dichroic mirror 34 that reflects the desired range of excitation wavelengths towards the object 10 to be imaged. The subsequent fluorescent signal includes a range of fluorescent wavelengths that pass through an objective lens 22 and are within a pass band of the dichroic mirror such that they pass through the dichroic mirror and are detected by the detector 26 and processed as previously described.

In the above described embodiments, the excitation unit, transmission unit, and detection unit have been described separately. However, it should be understood that these various units may either be combined in a single unitary system, or they may be provided as separate components as the disclosure is not so limited.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computing device or distributed among multiple computing devices. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a computing device may be embodied in any of a number of forms, such as a rack-mounted computer, a desktop computer, a laptop computer, or a tablet computer. Additionally, a computing device may be embedded in a device not generally regarded as a computing device but with suitable processing capabilities, including a Personal Digital Assistant (PDA), a smart phone or any other suitable portable or fixed electronic device.

Also, a computing device may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Such computing devices may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the disclosed embodiments may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present disclosure as discussed above. As used herein, the term "computer-readable storage medium" encompasses only a non-transitory computer-readable medium that can be considered to be a manufacture (i.e., article of manufacture) or a machine. Alternatively or additionally, the disclosed methods may be embodied as a computer readable medium other than a computer-readable storage medium, such as a propagating signal.

The terms "program" or "software" are used herein in a generic sense to refer to any type of computer code or set of computer-executable instructions that can be employed to program a computing device or other processor to implement various aspects of the present disclosure as discussed above. Additionally, it should be appreciated that according to one aspect of this embodiment, one or more computer programs that when executed perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Example: Targeted SWIR Imaging of a Liver with Near Infrared Dye

A mouse was previously implanted with a breast cancer tumor in the liver that showed significant over-expression of the HER2 receptor. Trastuzumab, a HER2-receptor targeting antibody, was conjugated to IRDye 800CW using a commercially available labeling kit. The dye-antibody conjugate was injected intraperitoneally into a mouse at a dose of 15 mg/kg body weight. Three days after the initial injection of the dye-antibody conjugate, the mouse was imaged using SWIR fluorescence detection.

As a control experiment, IRDye 800CW was conjugated to IgG, a non-specific antibody. The conjugate was injected into a second mouse model implanted with the same tumor in the same location.

Figure 4:
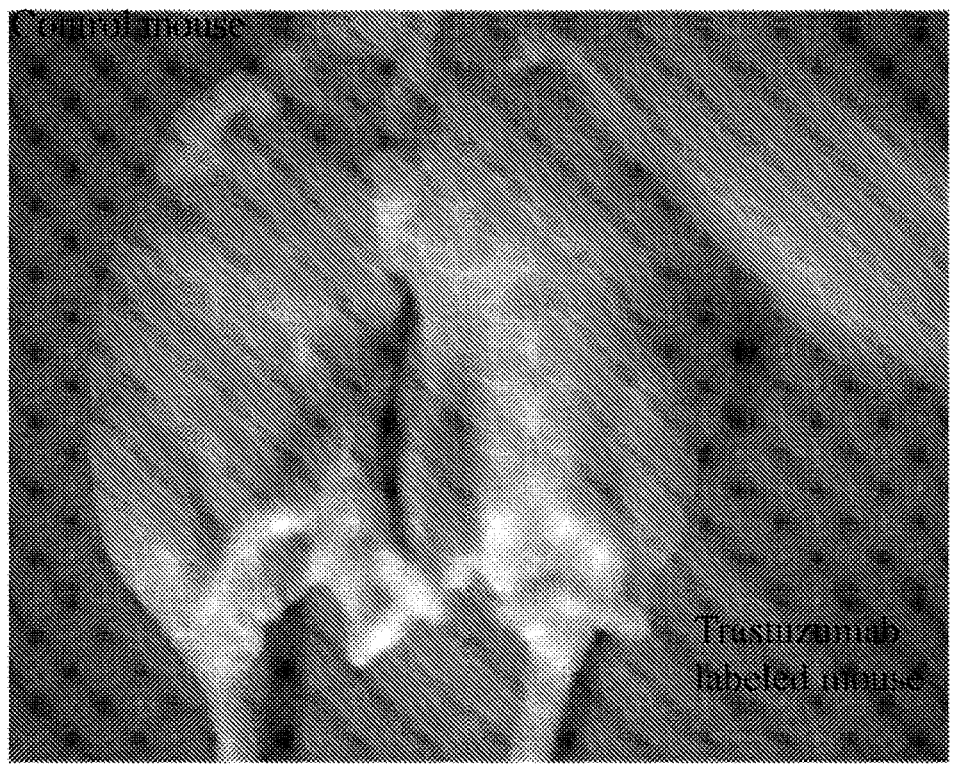
FIG. 4 is a white light image of a control animal model and diseased animal model.
Figure 5:
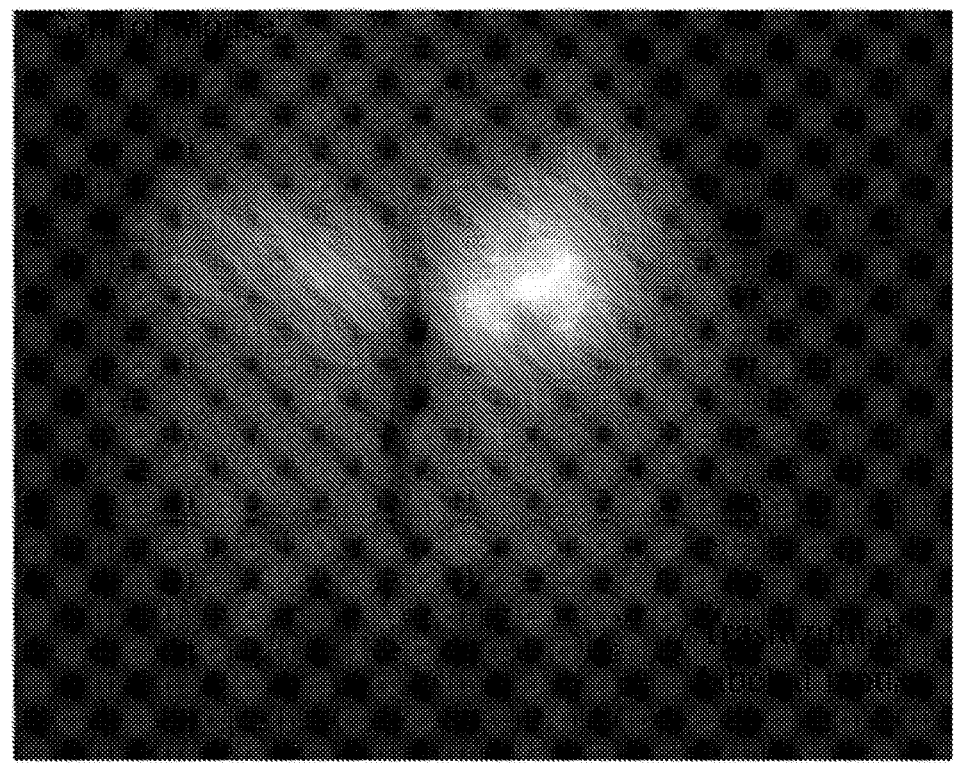
FIG. 5 is a fluorescence image of the control animal model and diseased animal model of FIG. 4.

FIG. 4 presents a white light image of both the control mouse on the left and the trastuzumab-labeled mouse on the right with room-lights on for positioning reference. FIG. 5 presents an SWIR image of both mice in the same positions. As seen in the image, a strong fluorescence signal, indicating the position of the tumor is seen in the trastuzumab-labeled mouse. In contrast, the IgG conjugate did not target the tumor, and no significant fluorescent signal was identified in the control mouse model.

Example: Absorption and Emission Spectra of Indocyanine Green

Figure 6:
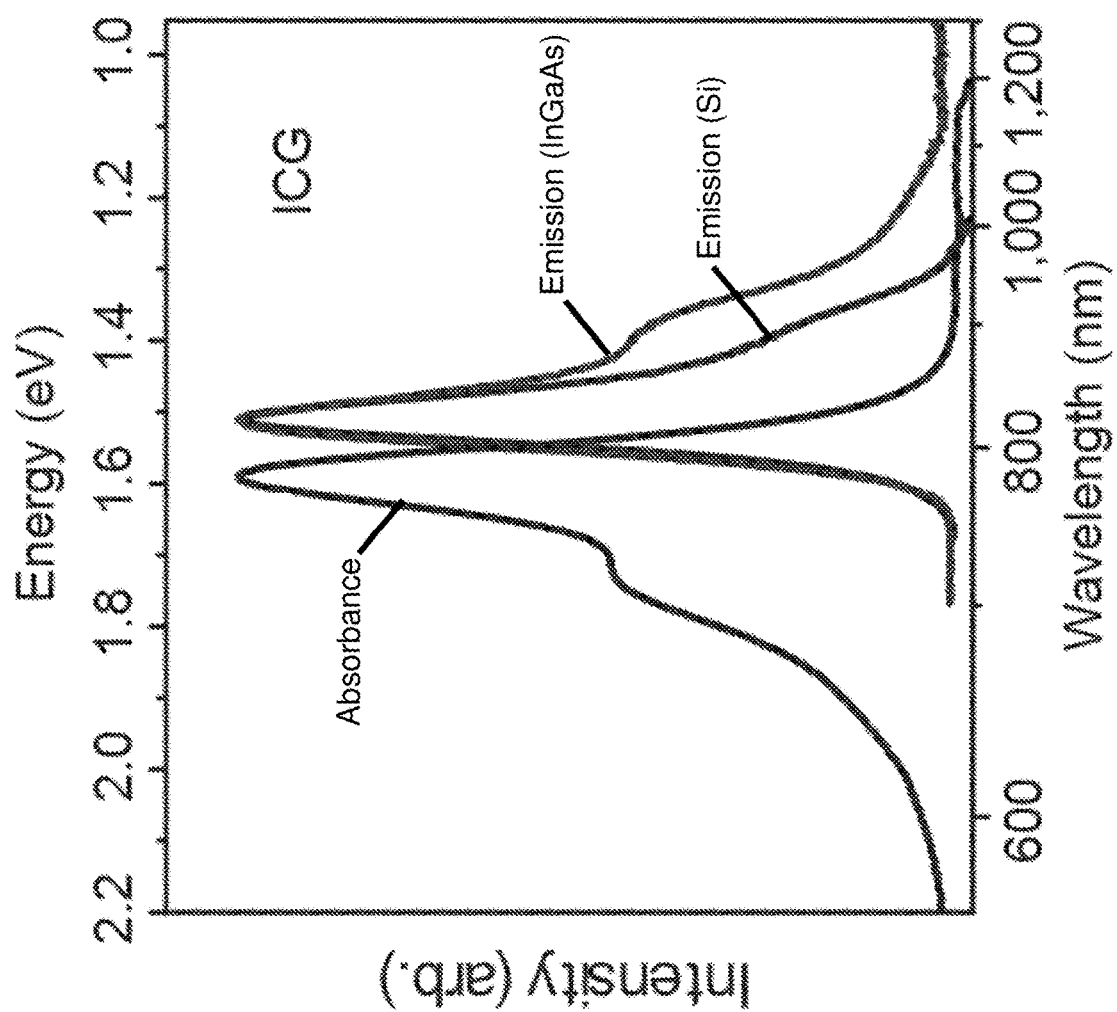
FIG. 6 is a graph of absorbance and corresponding emission spectra of indocyanine green as measured with different detectors.

The absorption maximum of indocyanine green is plotted in the graph shown in FIG. 6. The emission spectrum is also shown as measured by two different means of detection. First, the figure depicts an emission spectrum as measured by a typical silicon-based detection system, which due to the fundamental properties of silicon, has a relatively low sensitivity at wavelengths beyond 900 nm. In contrast the emission spectrum as measured by a thinned indium gallium arsenide (InGaAs)-based detection system shows a sensitivity in the range of wavelengths between 500-1700 nm. Comparison of the two emission spectra show that silicon-based detection systems under-detect the tail of the emission which has led to the common misconception that near infrared dyes, such as indocyanine green, have no emission at SWIR wavelengths and could not be used for SWIR imaging. Instead, as confirmed by these experiments, many near infrared dyes are expected to show significant detectable tails in the SWIR range.

Example: Intensity of ICG as Detected on an InGaAs Detector

Figure 7:
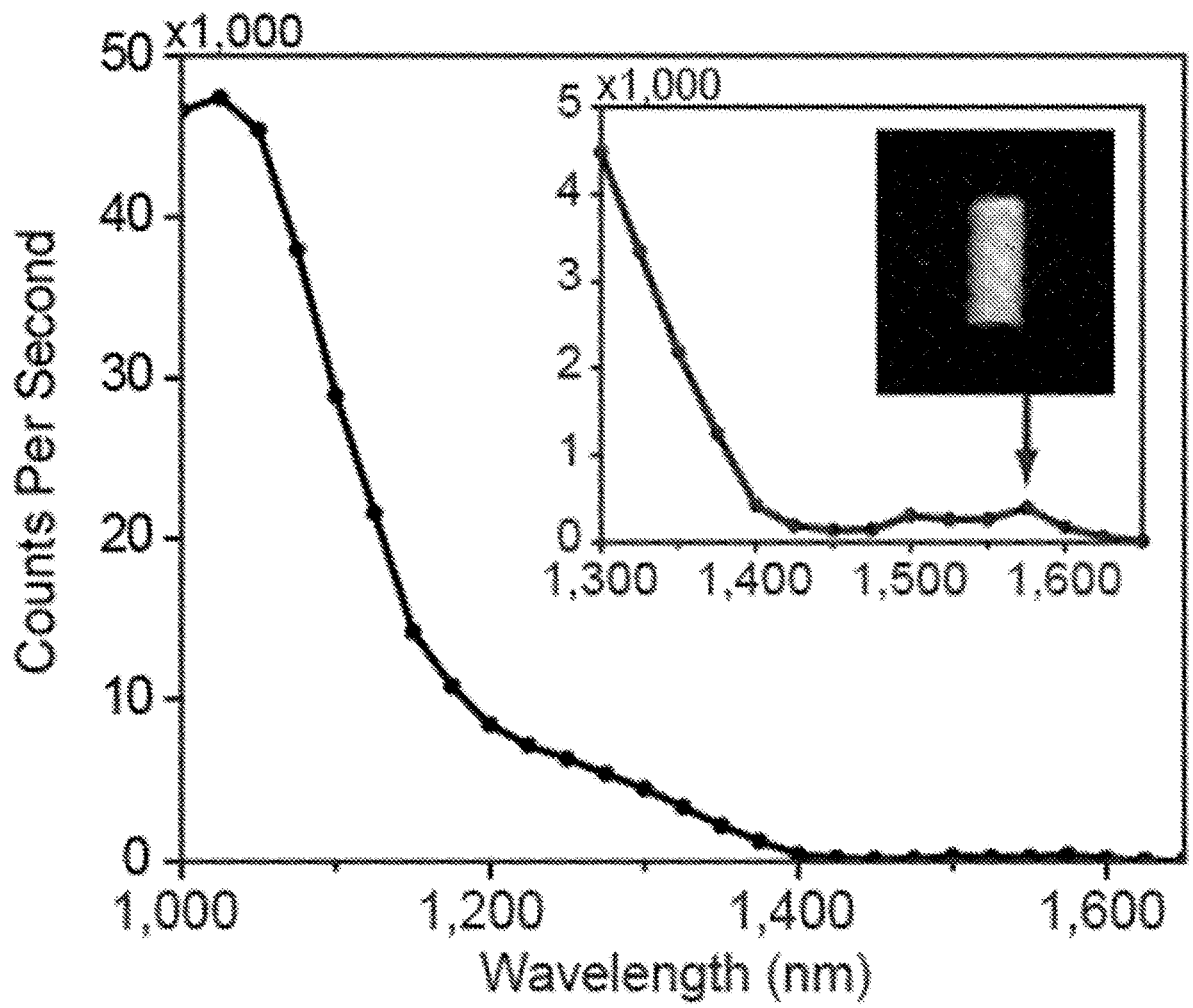
FIG. 7 is a graph of detected indocyanine green intensity measured with an InGaAs detector.

FIG. 7 shows the relative intensity of ICG as detected on an InGaAs detector. A vial with 0.027 mg/mL ICG dispersed in water was illuminated with approximately 50 mW/cm$^2$ of 808 nm excitation light and the emitted electromagnetic radiation was detected on the camera in 20 nm spectral bands centered every 25 nm between 900-1650 nm. Two 850 nm long pass filters were used to block reflected light from the 808 nm laser, and a VariSpec Liquid Crystal Tunable Filter was used to selectively pass the 20 nm spectral bands of ICG emission. Between 1000-1575 nm the detector responsivity is relatively flat and the intensity declines due to the decreasing emission of the dye. Intensity is low, but still detectable around 1450 nm due to strong reabsorption of the emission by the solvent (water), but the intensity slightly rises again between 1500-1600 nm as this reabsorption is less significant. Emission from the ICG is detectable across the entire sensitivity range of the InGaAs camera, with the inset image showing the vial of ICG as detected in the 20 nm spectral band centered at 1575 nm. Additionally, it is noted that the intrinsic ICG spectrum is larger than as measured in this experimental setup due to the water absorbing electromagnetic radiation in this spectral region.

Example: Detection of Indocyanine Green Across SWIR Wavelengths In Vivo

Figure 8:
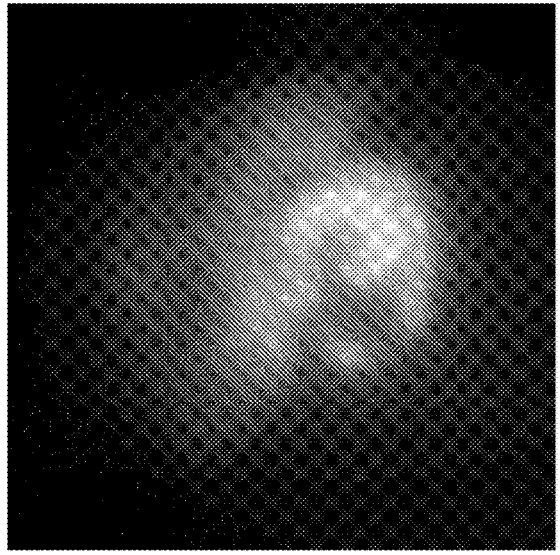
FIG. 8-FIG. 10 are fluorescence images at different wavelengths of a mouse liver and intestine labeled with indocyanine green.
Figure 9:
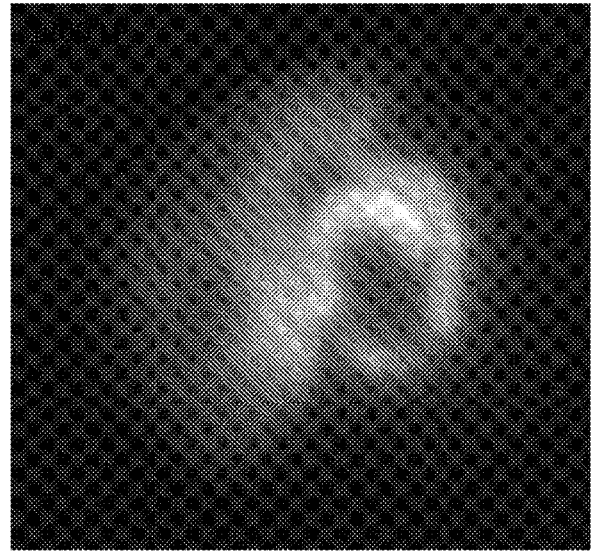
Figure 10:
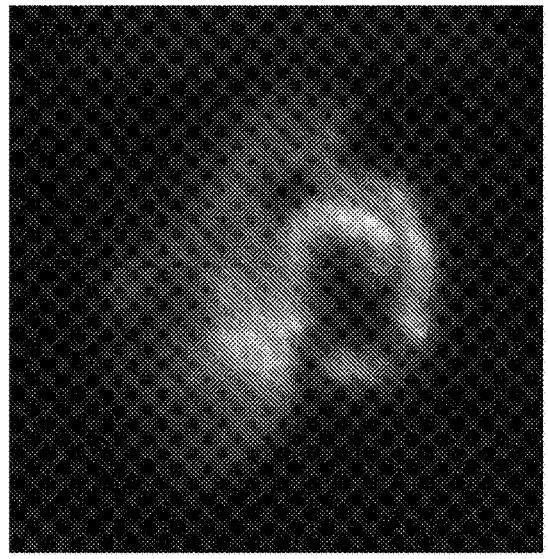

When injected into a living system, indocyanine green is metabolized by the liver and excreted by the liver and bile ducts by a process called hepatobiliary clearance. This process was observed, noninvasively, by injecting a solution of indocyanine green intravenously into a mouse and using an SWIR imaging system as described herein to observe the fluorescence of indocyanine green. The dye was injected at a dose of 1.7 mg/kg which is below the maximum recommended dose of indocyanine green in humans. Accumulation of indocyanine green in the liver of the mouse was observed using the SWIR fluorescence detection system. FIGS. 8-10 shows the liver and a portion of the small intestine of the mouse highlighted with fluorescence from indocyanine green as observed on the SWIR camera with a 900 nm longpass filter (detecting wavelengths 900-1650 nm), with a 1200 nm longpass filter (detecting wavelengths 1200-1650 nm), and with a 1500 nm longpass filter (detecting wavelengths 1500-1650 nm). Despite the fact that 1500 nm is far from the peak emission of indocyanine green, there is sufficient emission intensity from the tail of the emission peak in this wavelength region to obtain a SWIR fluorescence image. Separately, hepatobiliary excretion of ICG into the small intestine in a mouse was also imaged using a near video rate imaging of 19.7 frames per second using a 1200 nm long-pass filter, which enabled capturing the peristaltic movements of the small intestine. Although the frame rate was slower, 2.0 frames per second, it was possible to image the ICG clearance using a 1500 nm long-pass filter, capturing wavelengths between roughly 1500 and 1620 nm.

Example: Noninvasive Brain Vasculature Imaging

Figure 11:
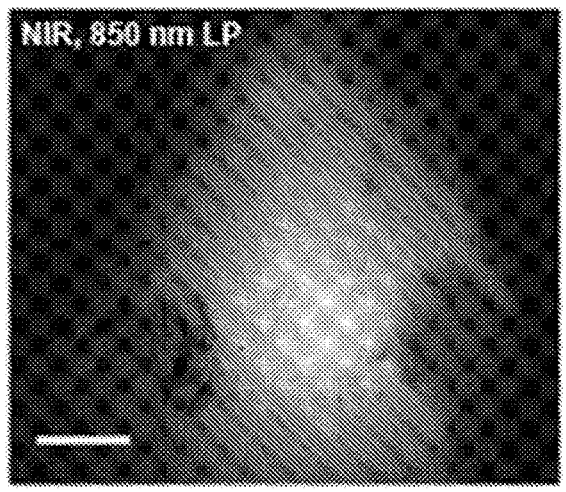
FIG. 11 is a fluorescence image of a mouse head using a near infrared silicon based detection system.
Figure 12:
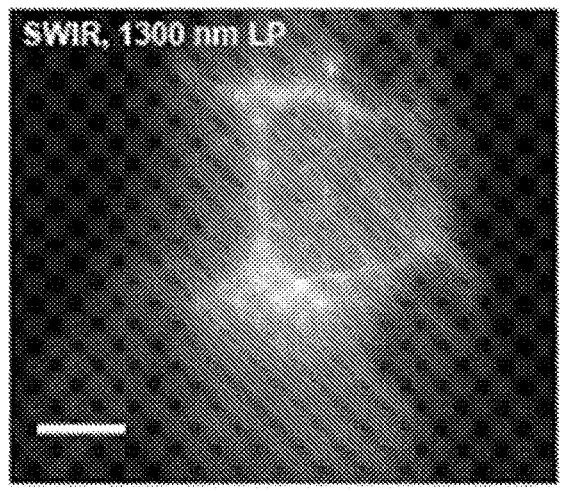
FIG. 12 is a fluorescence image of a mouse head using a short wave InGaAs based detection system.

FIGS. 11 and 12 present imaging of ICG in the NIR and SWIR respectively using high-contrast mesoscopic imaging of brain vasculature in a mouse through intact skin and skull. Specifically, an aqueous solution of ICG was injected into the tail vein of a mouse at a dose of 0.2 mg/kg, which is within the recommended dose for humans (0.2-0.5 mg/kg recommended, 5 mg/kg maximum). The mouse was then illuminated with 50-70 mW/cm$^2$ of 808 nm excitation light, staying below the maximum permissible exposure limit (330 mW/cm$^2$ for 808 nm continuous wave light). The mouse was then noninvasively imaged using the resulting fluorescence captured on a silicon camera at NIR wavelengths, and on an InGaAs camera at SWIR wavelengths between 1300 nm and 1620 nm, the detection cutoff of the cooled SWIR camera. The contrast within a region of interest containing the brain vasculature in the NIR image and the SWIR image was calculated using the coefficient of variation, defined as the standard deviation of pixel intensity normalized to the mean pixel intensity. The SWIR image contrast was nearly 50% greater with a value of 0.29 as compared to the NIR image with a contrast value of 0.20. Furthermore, the apparent vessel width for a brain vessel was measured using the full width at half maximum of a two-Gaussian fit to the intensity profile across the vessel of interest. The apparent vessel width measured for the NIR image was over twice as wide in as the apparent width measured in the SWIR image with values of 430 μm and 210 μm, respectively. This confirms that contrast and resolution of fine vasculature structure can be greatly improved while using FDA-approved ICG contrast by simply switching the detection wavelength from traditional NIR imaging using a silicon camera, to detection beyond 1300 nm on an InGaAs SWIR camera.

Example: Intravital Brain Vasculature Imaging

Figure 13:
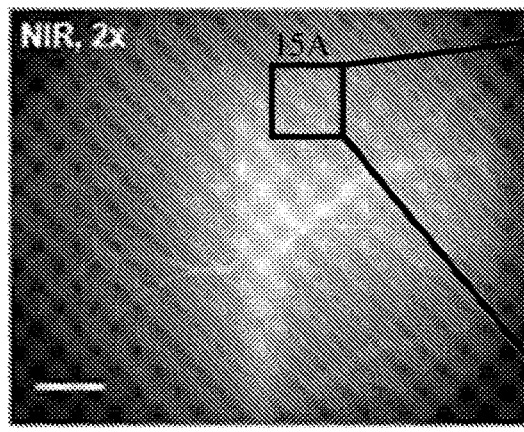
FIGS. 13-13A are fluorescence images of brain vasculature using a near infrared silicon based detection system through a cranial window implanted in a mouse.
Figure 13A:
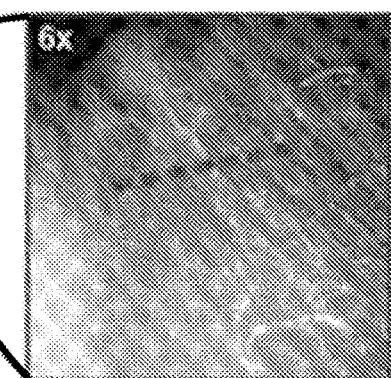
Figure 14:
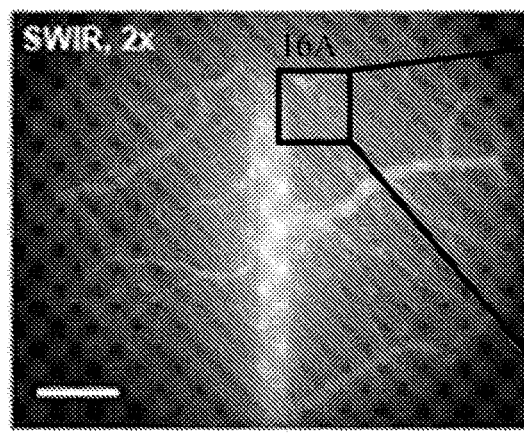
FIGS. 14-14A are fluorescence images of brain vasculature using a short wave InGaAs based detection system through a cranial window implanted in a mouse.
Figure 14A:
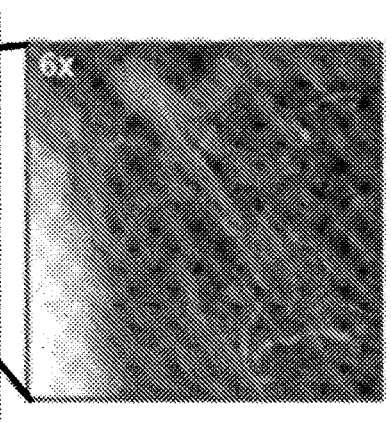

To further show the improved contrast of SWIR detection as compared to NIR detection for microscopic imaging, intravital brain vasculature imaging was performed in the noted wavelength ranges. Specifically, ICG was incorporated into polyethylene glycol-phospholipids to increase the blood half-life, which is typically limited to 3-4 min. An aqueous solution including these micelles was injected into the tail vein of a mouse with an implanted cranial window. A microscope was then used to image the fluorescence of the ICG phospholipid micelles in the brain vasculature with both NIR detection and a 1300 nm long-pass SWIR detection. Images of the entire cranial window at two times magnification showed the ability to resolve nearly all the same vessels using either NIR or SWIR imaging, see FIGS. 13 and 14 respectively. However, the overall contrast was 1.4 times greater for the SWIR image (standard deviation/mean equals 0.24 for NIR versus 0.33 for SWIR). Additionally, using a higher magnification, 6 times, reveals that this contrast improvement using SWIR imaging enables the resolution of vessels which, due to the high label density of surrounding vessels, are indistinguishable from background signal using NIR image, see FIGS. 13A and 14A.

Example: Real-Time SWIR Fluorescence Imaging In Vivo Using ICG

Figure 15:
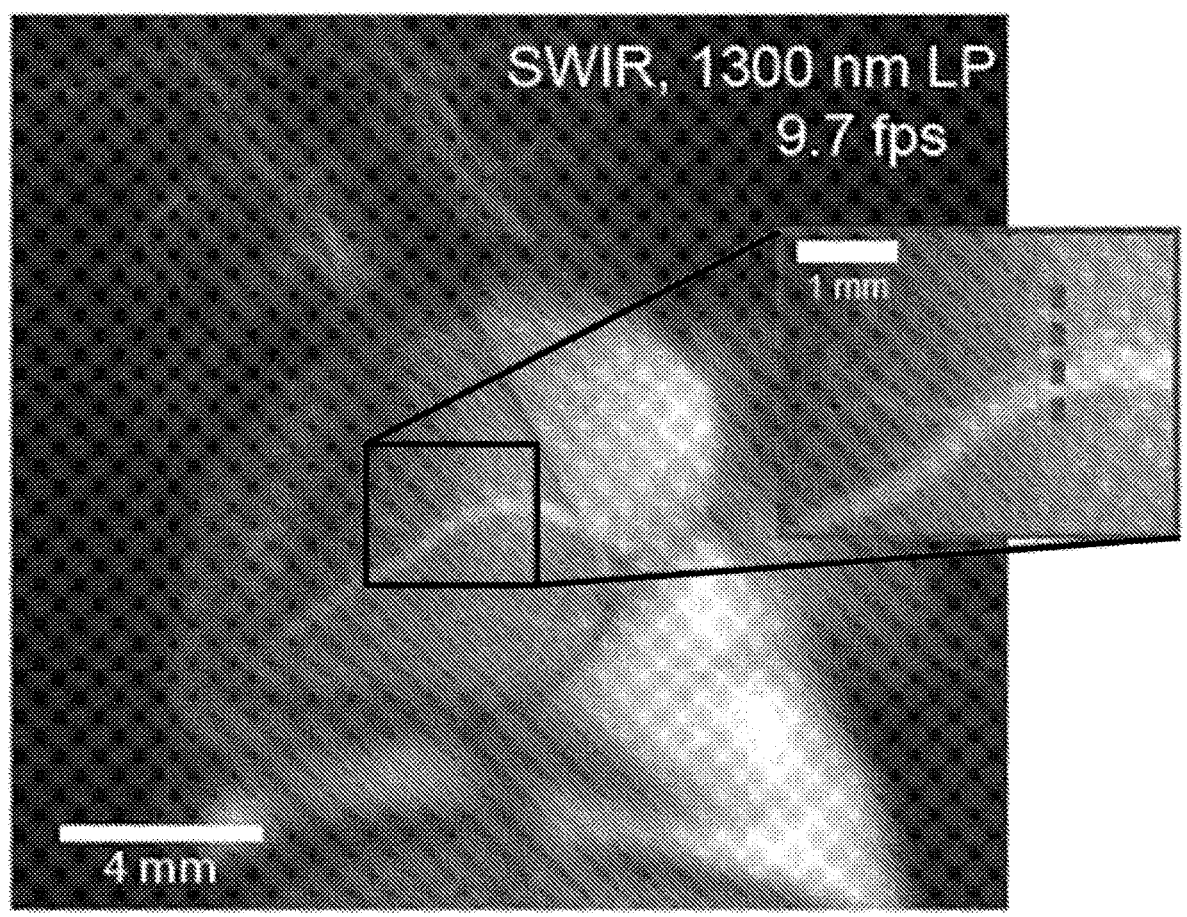
FIG. 15 is a fluorescence image of a mouse heart using a short wave InGaAs based detection system.

Angiography in a beating mouse heart was done to show that SWIR emission of ICG is sufficiently bright for real-time imaging with high frame rates, as would be used in fluorescence-guided surgery. To perform the angiography, diffuse 808 nm excitation light was emitted towards the beating mouse heart and a 1300 nm long-pass emission filter was used with an InGaAs SWIR camera. During image capture, it was possible to image the vasculature of the beating heart at speeds of 9.7 frames per second while resolving fine vessels on the exterior surface against the underlying contrast, FIG. 15. At a small contrast cost, it was also possible to image the heart vasculature at a faster speed of 15 frames per second using an 1150 nm long-pass emission filter.

Example: Imaging of Lymphatic Flow Using ICG

Figure 16:
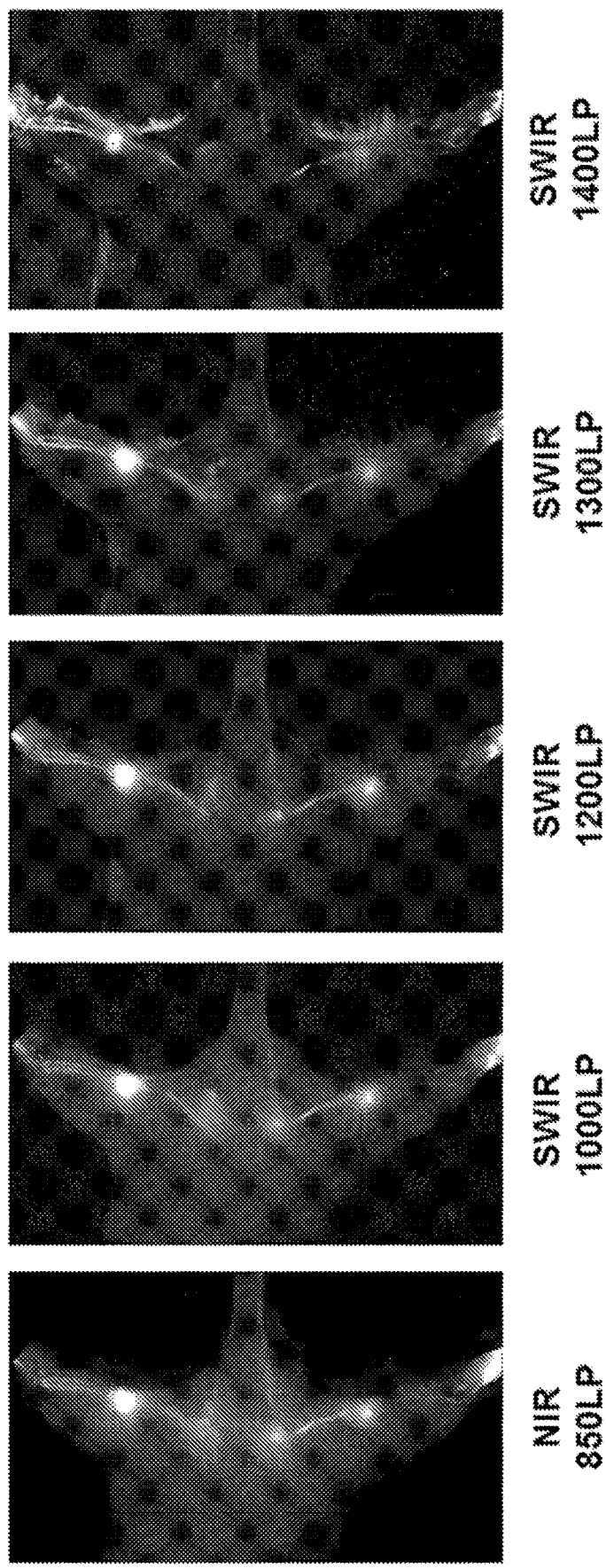
FIG. 16 is a series of fluorescence images of lymphatic flow within a mouse using different wavelengths.

In yet another example, lymphatic flow in a mouse was noninvasively imaged using ICG. An aqueous solution of ICG was subcutaneously injected into the hind paws and tail of the mouse. ICG fluorescence was then imaged through the intact skin to visualize lymphatic clearance. The fluorescence signal was imaged with a commercial Navitar lens with 850 nm, 1000 nm, 1200 nm, 1300 nm, 1400 nm longpass dielectric filters. Using these various bandpass filters across the SWIR frequency range, the lymph vessels and nodes were visible with ICG contrast up to approximately 1400 nm, at which point only the vessels and superficial nodes were visible and the signal of deeper lymph nodes became attenuated due to a water absorption band at 1450 nm, see FIG. 16.

Example: In Vivo Targeted Imaging with IRDye 800CW

Figure 17A:
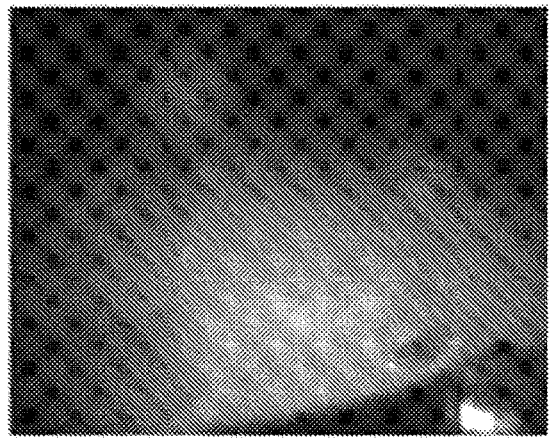
FIG. 17A is an image of a mouse head.
Figure 17B:
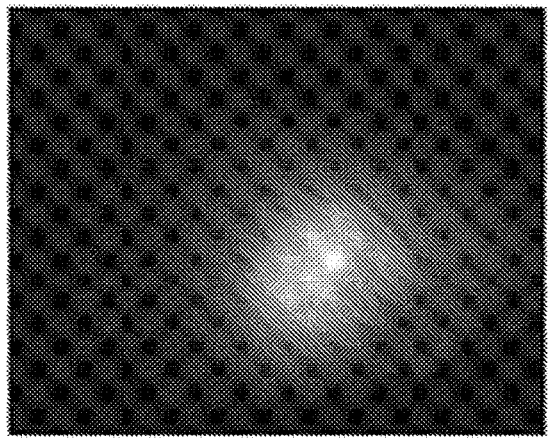
FIG. 17B is a fluorescence image of the mouse head of FIG. 17A using IRDye800-trastuzumab.
Figure 17C:
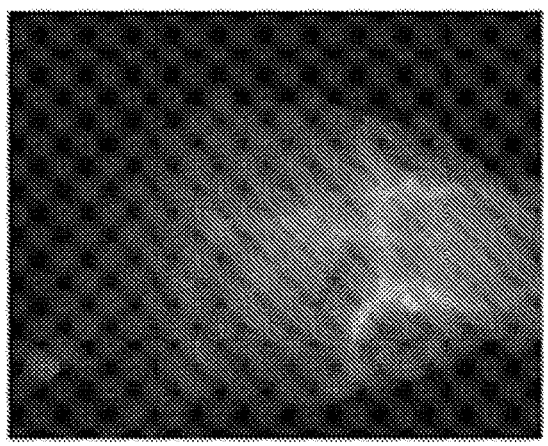
FIG. 17C is a fluorescence image of the mouse head of FIG. 17A using IRDye800-Peg.
Figure 17D:
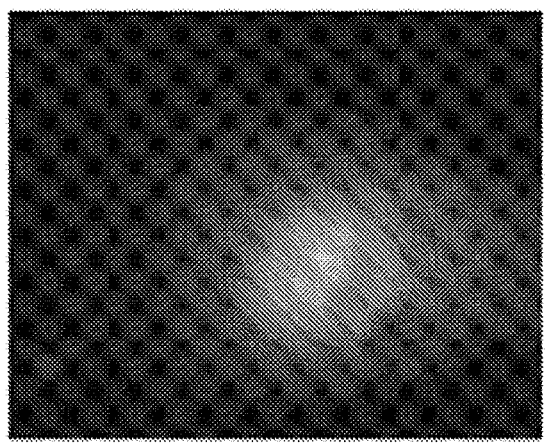
FIG. 17D is a composite false color image of the fluorescence images shown in FIGS. 17B and 17C.

Molecular targeted fluorescence imaging in the SWIR using the NIR dye IRDye 800CW was performed. A commercially-available labeling kit was used to conjugate IRDye 800CW with the tumor-targeting antibody trastuzumab. The dye-antibody conjugate was injected into a mouse model implanted with human BT474 breast cancer cells in the brain. A room light reflectance image of the mouse head is shown in FIG. 17A. The mouse head was then noninvasively imaged with the SWIR fluorescence emitted from the IRDye 800CW-labeled tumor, see FIG. 17B. Subsequently, IRDye 800CW conjugated to polyethylene glycol (PEG), highlighting brain vasculature surrounding the tumor, see FIG. 17C. A multi-color functional image of the brain was then generated by temporally resolving the two labels, i.e. by assigning different colors before and after the addition of IRDye 800CW PEG, see FIG. 17D.

Example: Contrast Versus Depth

FIGS. 18A-18D are a series of fluorescence images taken of quantum dot labeled cells of a mouse liver, taken with a 10× objective at a depth of 80 µm. The images were acquired with 50 nm broad bandpass (BP) filters with a center wavelength at 1000 nm, 1200 nm, 1450 nm, and 1600 nm as indicated in the images. The insets show a close-up of the black square in the corresponding image. All images exhibit the same intensity scale. Scale bars represent 100 um.

FIG. 19 is a graph of observed contrast plotted as a function of wavelength for images taken using bandpass filters centered every 50 nm between 950 nm and 1600 nm. FIG. 20 is a graph of penetration depth as a function of wavelength for images acquired with a 10× objective. The dashed line marks a penetration depth of 80 µm, and the crosses on the graph indicate the wavelength positions of the images presented in FIGS. 18A-18B.

Example: Autofluorescence of Tissue Using SWIR

Figure 21:
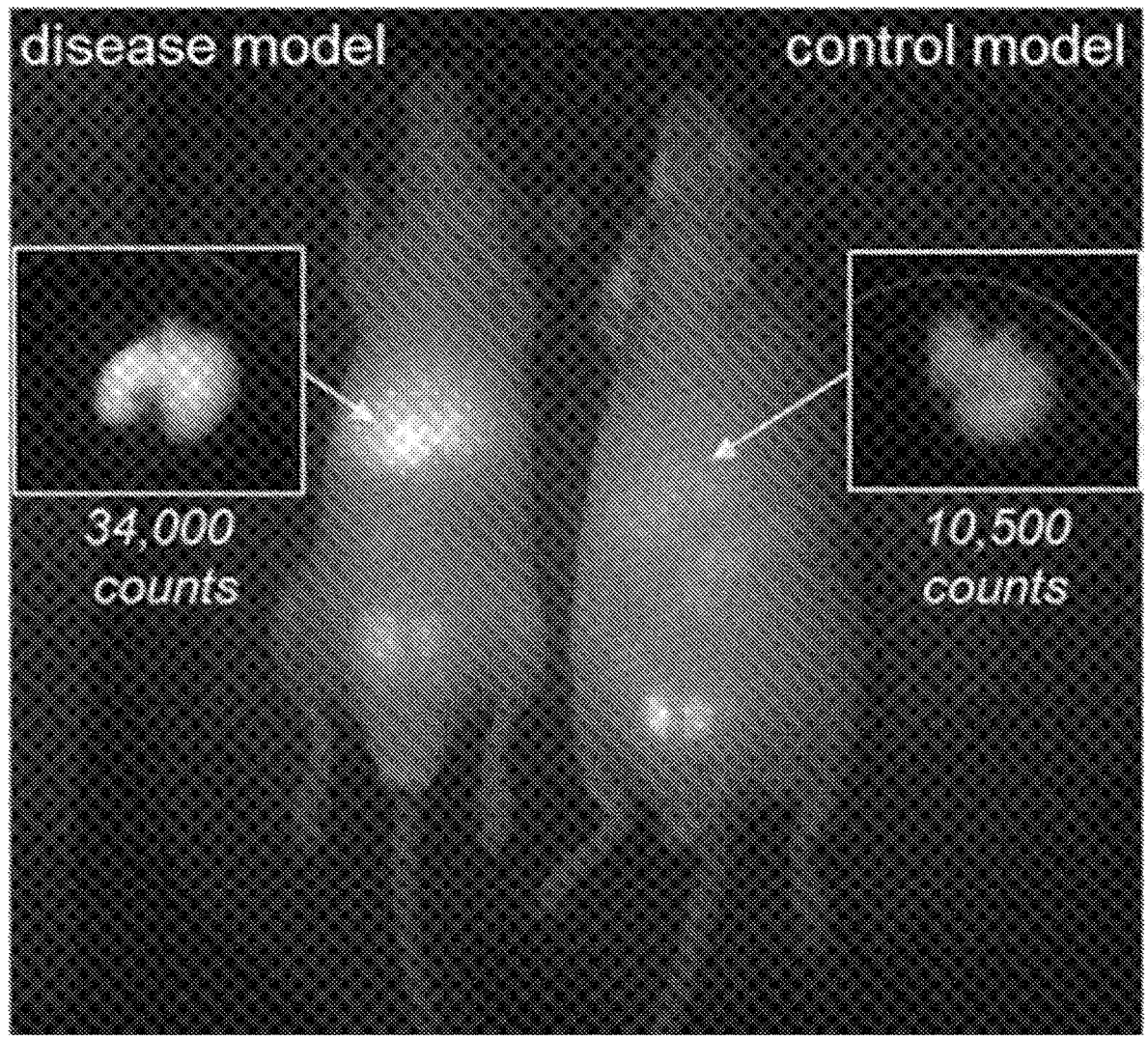
FIG. 21 is a fluorescence image comparing autofluorescence in a diseased and control animal model.
Figure 22:
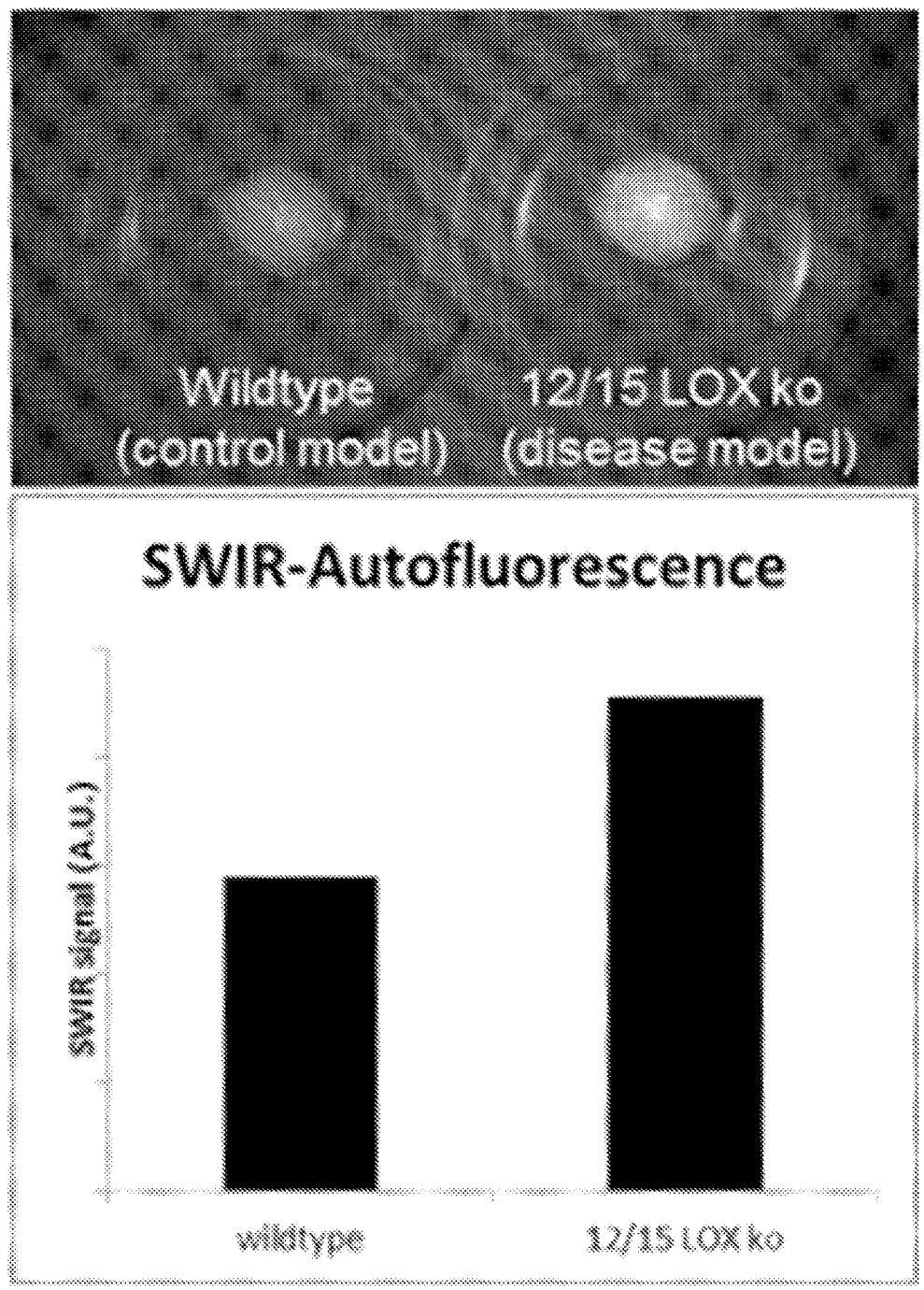
FIG. 22 compares the autofluorescence signals measured in the brain of a diseased animal model and control animal model.

SWIR imaging was conducted on control mice and mice with dysregulated autophagy, a major intracellular degradation pathway that may be linked to an increasing number of neurodegenerative diseases including Huntington's, Parkinson's, and Alzheimer's disease. As shown in FIG. 21, the disease mouse model exhibited enhanced SWIR autofluorescence in the cirrhotic livers as compared to the control model. Similarly, an enhanced SWIR autofluorescence signal was observed in the brain of the diseased model as compared to the control model as shown in FIG. 22. Without wishing to be bound by theory, the increased observed contrast is due to most healthy tissues having very little autofluorescence at electromagnetic wavelengths between about 1000 and 2000 nm. However, some disease conditions can elevate SWIR autofluorescence signals in specific organs, or other biologic structures, providing disease-correlated contrast in an SWIR image.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A system comprising:
an excitation source configured to emit electromagnetic radiation within an absorption spectrum of a fluorescent component of a fluorescent probe, wherein the fluorescent probe includes the fluorescent component attached to a carrier, wherein the fluorescent component fluoresces over a first range of wavelengths and the carrier autofluoresces over a second range of wavelengths at least partially overlapping the first range of wavelengths, wherein a ratio of an intensity of the fluorescence and a corresponding intensity of the autofluorescence at a tail portion fluorescent emission wavelength of the fluorescent component is greater than a ratio of the intensity of the fluorescence and the corresponding intensity of the autofluorescence at a peak fluorescent emission wavelength of the fluorescent component, and wherein the carrier comprises nanoparticles, antibodies, proteins, DNA, and/or small molecules;
a detector configured to detect electromagnetic radiation within the tail portion of the fluorescence of the fluorescent component; and
a processor configured to detect a subject condition based at least in part on the tail portion of the fluorescence of the fluorescent component.

2. The system of claim 1, wherein the detector outputs a detected tail portion signal to the processor.

3. The system of claim 2, wherein the processor compares the detected tail portion signal to an intensity threshold to detect the subject condition.

4. The system of claim 1, wherein the subject condition is cirrhotic liver disease.

5. The system of claim 1, further comprising a display, wherein the detector outputs a detected tail portion signal to the display.

6. The system of claim 1, wherein the excitation source emits electromagnetic radiation at wavelengths less than or equal to 900 nm.

7. The system of claim 1, wherein the tail portion fluorescent emission wavelength of the fluorescent component includes wavelengths greater than or equal to 900 nm.

8. The system of claim 1, wherein the tail portion fluorescent emission wavelength of the fluorescent component includes wavelengths less than or equal to 2000 nm.

9. The system of claim 1, wherein the detector detects electromagnetic radiation with wavelengths less than or equal to 2000 nm.

10. The system of claim 1, wherein the detector detects electromagnetic radiation with wavelengths greater than or equal to 900 nm.

11. The system of claim 1, comprising the fluorescent probe.

12. The system of claim 1, wherein the detector detects electromagnetic radiation in a frequency range between or equal to 1400 nm and 1500 nm.

13. A method comprising:
exposing a portion of tissue including a fluorescent probe to an excitation source of the fluorescent probe, wherein the fluorescent probe includes a fluorescent component attached to a carrier, wherein the fluorescent component fluoresces over a first range of wavelengths and the carrier autofluoresces over a second range of wavelengths at least partially overlapping the first range of wavelengths, wherein a ratio of an intensity of a tail portion of the first range of wavelengths and a corresponding intensity of the carrier autofluorescence is greater than a ratio of an intensity of a peak fluorescent emission wavelength of the fluorescent component and a corresponding intensity of the carrier autofluorescence, and wherein the carrier comprises nanoparticles, antibodies, proteins, DNA, and/or small molecules; and
detecting the tail portion of the fluorescence of the fluorescent component.

14. The method of claim 13, wherein the tail portion of the fluorescence of the fluorescent component has a wavelength that is greater than or equal to 900 nm.

15. The method of claim 14, wherein the tail portion of the fluorescence of the fluorescent component has a wavelength that is less than or equal to 2000 nm.

16. The method of claim 14, wherein the autofluorescence of the carrier has a peak autofluorescent emission wavelength below 900 nm.

17. The method of claim 14, wherein the peak fluorescent emission wavelength of the fluorescent component is below 900 nm.

18. The method of claim 13, further comprising determining a condition of a subject based on the detected tail portion of the fluorecence of the fluorescent component.

19. The method of claim 18, wherein the condition of the subject includes cirrhotic liver disease.

20. The method of claim 13, further comprising administering a therapeutic amount of the fluorescent probe.

21. The method of claim 13, wherein the fluorescent component comprises at least one of indocyanine green, Fluorescein, methylene blue, cyanine5, cyanine5.5, cyanine7, cyanine7.5, silicon rhodamine, 5-ALA, IRDye 700, IRDye 800CW, IRDye800 RS, E350, squarylium dye, phthalocyanine, porphyrin derivative, and borondipyrromethane.

22. The method of claim 13, wherein detecting the tail portion includes detecting electromagnetic radiation in a frequency range between or equal to 1400 nm and 1500 nm.

23. The system of claim 11, wherein the fluorescent probe comprises at least one of indocyanine green, Fluorescein, methylene blue, cyanine5, cyanine5.5, cyanine7, cyanine7.5, silicon rhodamine, 5-ALA, IRDye 700, IRDye 800CW, IRDye 800RS, E350, squarylium dye, phthalocyanine, porphyrin derivative, and borondipyrromethane.

* * * * *

UNITED STATES PATENT AND TRADEMARK OFFICE
CERTIFICATE OF CORRECTION

PATENT NO. : 11,579,088 B2
APPLICATION NO. : 16/083603
DATED : February 14, 2023
INVENTOR(S) : Moungi G. Bawendi et al.

It is certified that error appears in the above-identified patent and that said Letters Patent is hereby corrected as shown below:

In the Claims

At Column 20, Claim 18, Line 9:
"...portion of the fluorecence..."
Should read:
--...portion of the fluorescence...--

At Column 20, Claim 23, Line 30:
"...IRDye 800RS..."
Should read:
--...IRDye 800 RS...--

Signed and Sealed this
Twentieth Day of February, 2024

Katherine Kelly Vidal
*Director of the United States Patent and Trademark Office*